United States Patent [19]

Callahan et al.

[11] Patent Number: 5,061,260
[45] Date of Patent: Oct. 29, 1991

[54] NONDISPOSABLE DIAPER

[76] Inventors: Joanne Callahan; Christine Houle, both of 10986 N. 218 St. Ct., Scandia, Minn. 55073

[21] Appl. No.: 558,100
[22] Filed: Jul. 26, 1990
[51] Int. Cl.⁵ .............................................. A61F 13/15
[52] U.S. Cl. ................................... 604/378; 604/358; 604/385.1
[58] Field of Search ............. 604/366, 378, 383, 385.1, 604/358

[56] References Cited

U.S. PATENT DOCUMENTS 3,409,012 11/1968 Seltzer .................................. 604/378
4,762,521 8/1988 Roessler et al. ................... 604/385.1

*Primary Examiner*—Randy Citrin Shay
*Assistant Examiner*—G. Gualtieri

*Attorney, Agent, or Firm*—Merchant, Gould, Smith, Edell, Welter & Schmidt

[57] ABSTRACT

The present invention provides a nondisposable diaper which includes a top section and a bottom section. The top and bottom sections are attached by discontinuous perimeter stitching along perimeter ends of the top and bottom section. The perimeter stitching defines first and second openings which permit air to more freely flow between inside surfaces of the top and bottom sections and thereby permit the nondisposable diaper to dry faster. The top and bottom section further include respective outside and inside layers with an absorbency pad secured between the outside and inside layers. The absorbency pad is secured within the nondisposable diaper so that the stitching is not exposed to outside contact.

23 Claims, 3 Drawing Sheets

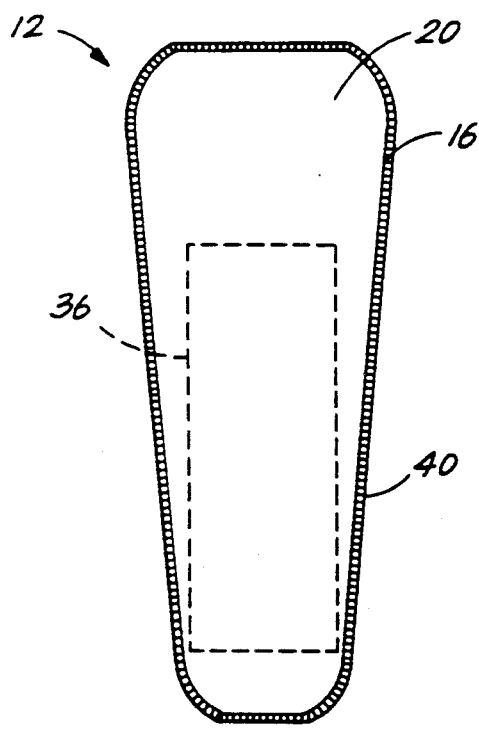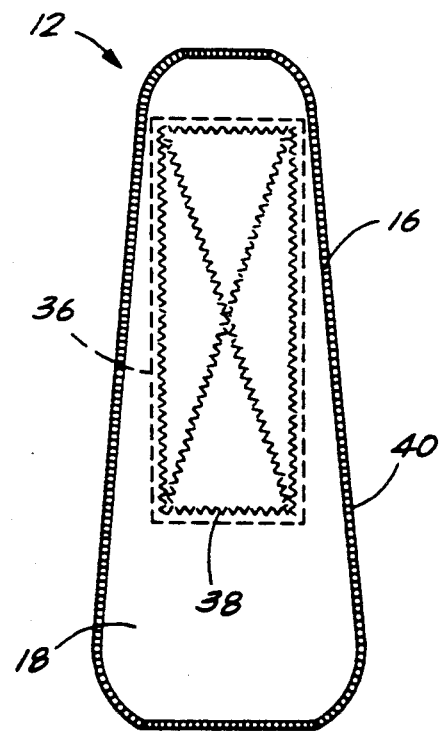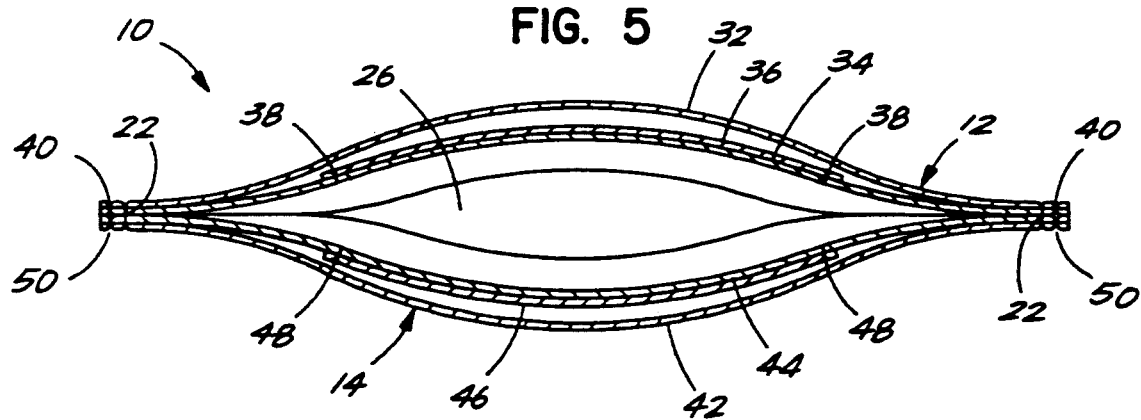

NONDISPOSABLE DIAPER

FIELD OF INVENTION

The present invention relates to an improved nondisposable diaper.

BACKGROUND OF THE INVENTION

With the ever present waste management problem, the baby care industry has felt a long and increasing need for new and improved nondisposable diapers. For example, some publications have estimated that approximately 18 billion plastic diapers are buried in landfills each year, and that disposable diapers constitute approximately 30% of the total nonbiodegradable materials buried in landfills in the United States.

Part of the problem is that the baby care industry has made few improvements to enhance the ease of use and durability of the conventional nondisposable diapers. The present invention provides such improvements and accordingly should provide additional encouragement to parents to switch from using disposable diapers, which have created an environmental problem, to a nondisposable diaper.

For example, the present invention provides a nondisposable diaper in which critical stitching is enclosed and thus protected against wear and tear from outside contact. Also, by not exposing such seams to the baby's bottom, the nondisposable diaper in the present invention is more comfortable for the baby. Also, the present invention provides an improved design which permits the nondisposable diaper to dry faster and more efficiently. Decreased drying time translates into energy savings. Also, the nondisposable diaper according to the present invention requires less material which means that more diapers may be washed in one drying load.

A related problem often encountered with conventional nondisposable diapers is that because they do not dry during a typical drying cycle, they remain somewhat damp while stored. A damp diaper is more susceptible to molding and rotting, and thus typically will not last as long. The present invention helps to eliminate these and other problems associated with conventional nondisposable diapers.

SUMMARY OF THE INVENTION

Under an embodiment of the present invention, the nondisposable diaper comprises a top section which has perimeter ends, and an inside surface and an outside surface; a bottom section which has perimeter ends, and an inside surface and an outside surface, the respective inside surfaces of the top and bottom sections facing one another; and structure for attaching the top section to the bottom section along the respective perimeter ends in a discontinuous manner thus defining at least one opening between the respective top and bottom sections, the opening permitting air to more freely enter and flow between the respective inside surfaces of the top and bottom sections and thereby permitting the nondisposable diaper to dry faster, for example, during a drying cycle.

These and other various advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 3 shows a top view of top section 12 (or its mirror image bottom section 14) shown in FIG. 2.

FIG. 4 is a bottom view of top section 12 (or its mirror image bottom section 14) shown in FIG. 2.

FIG. 5 is a cross-sectional view of the diaper shown in FIG. 1, taken along lines 5—5.

DETAILED DESCRIPTION OF THE PREFERRED EMBODIMENTS

Figure 6:
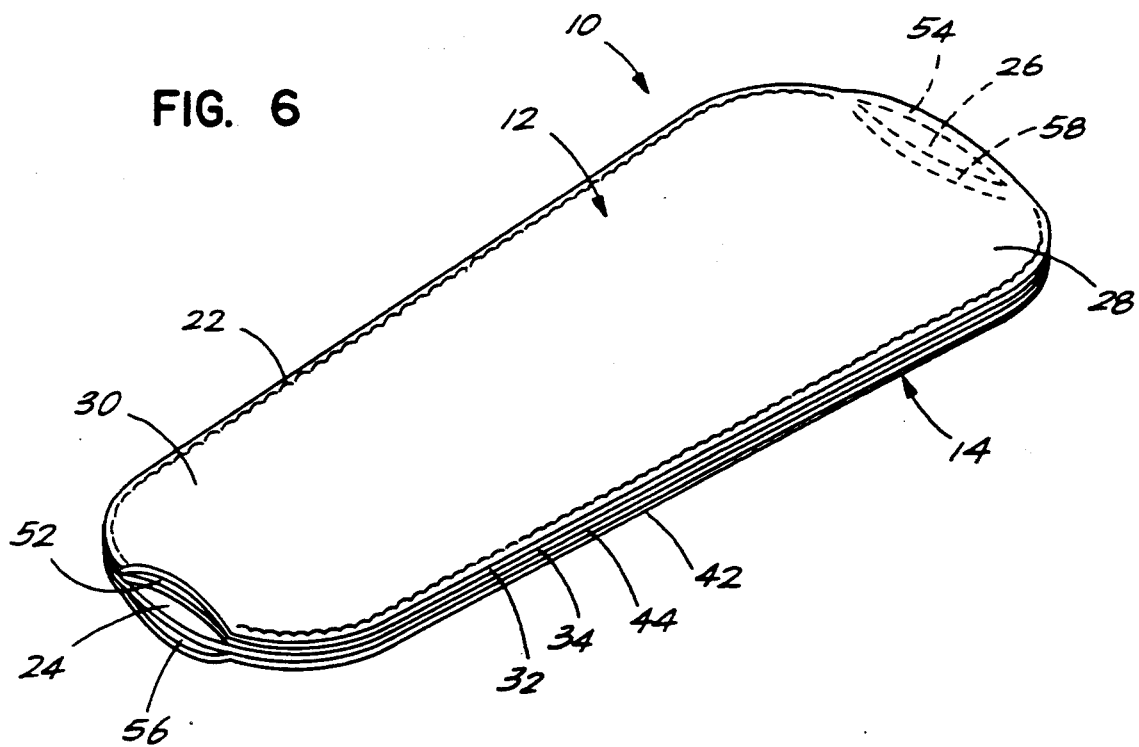
FIG. 6 is an alternative preferred embodiment of the nondisposable diaper shown in FIGS. 1-5.

Referring now to drawings, FIGS. 1-5 disclose a nondisposable diaper constructed according to the preferred embodiment of the present invention. FIG. 6 discloses an alternative preferred embodiment of the nondisposable diaper shown in FIGS. 1-5. It should be noted that like reference numerals designate corresponding elements throughout the drawings.

Figure 1:
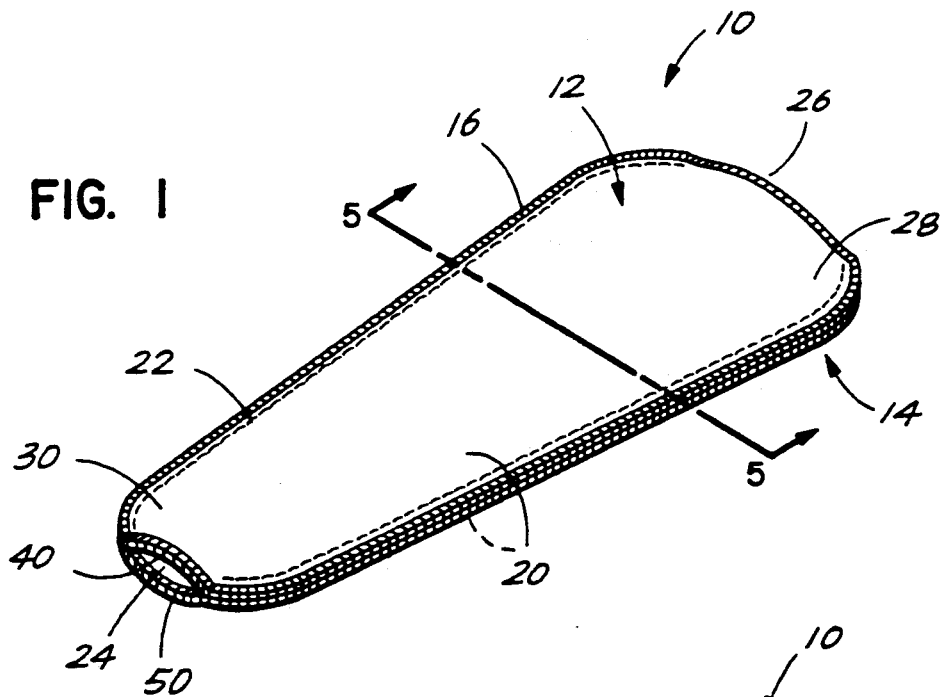
FIG. 1 is a perspective view of a nondisposable diaper constructed according to the preferred embodiment of the present invention.
Figure 2:
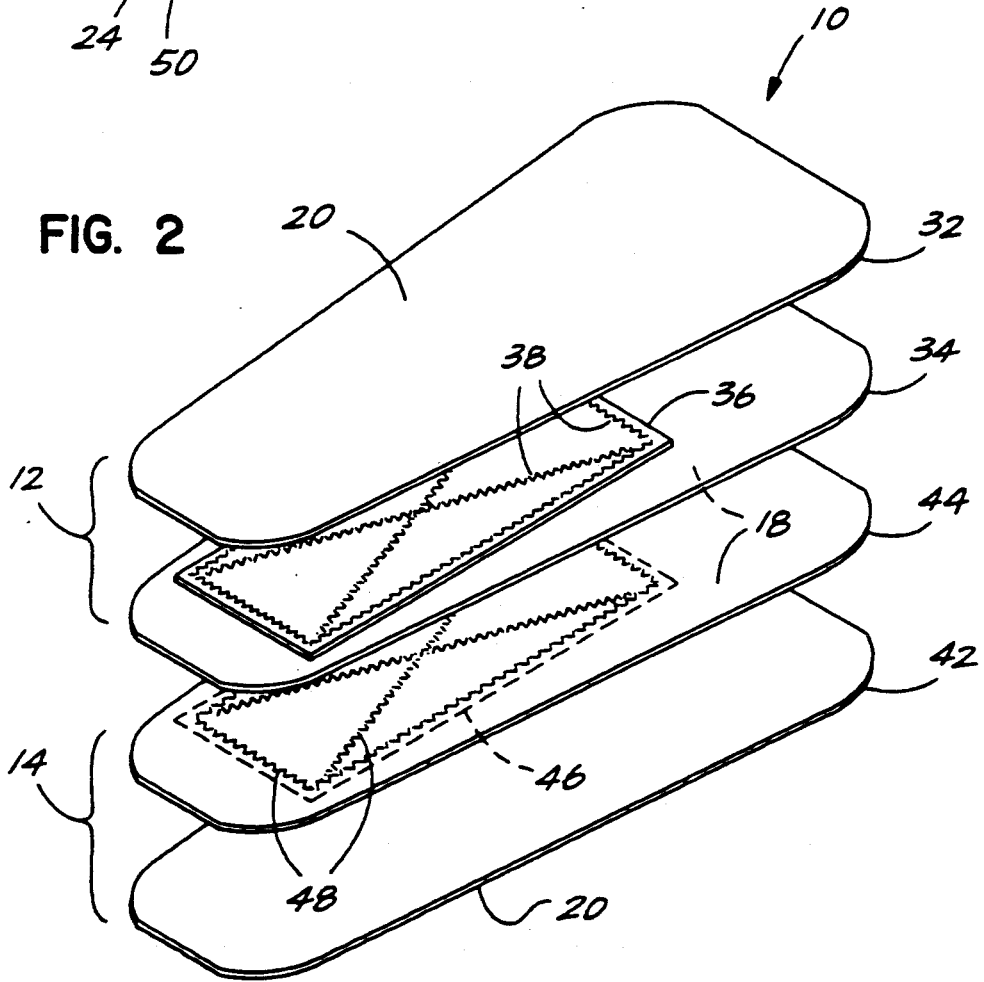
FIG. 2 is an exploded perspective view of a nondisposable diaper constructed according to the preferred embodiment of the present invention.

Referring to FIGS. 1, 2 and 5, the nondisposable diaper 10 according to the present invention includes a top section 12 and a bottom section 14. In the preferred embodiment, the top and bottom sections 12, 14 are symmetrical, each having corresponding perimeter ends 16 and inside surfaces 18 and outside surfaces 20. The respective inside surfaces of the top and bottom sections face one another.

The nondisposable diaper further includes attachment means 22 for attaching the top section 12 to the bottom section 14 along their respective perimeter ends 16 in a discontinuous manner. The attachment means may comprise discontinuous perimeter stitching 22 as shown in FIGS. 1 and 5. The discontinuous perimeter stitching defines at least one opening 24 between the respective top and bottom sections 12, 14. The opening 24 permits air to more freely enter and flow between the respective inside surfaces 18 of the top and bottom sections during, for example, a drying cycle. This permits the nondisposable diaper 10 to dry faster and more efficiently and thereby helps to eliminate the problem encountered when the diaper does not dry during the typical drying cycle which is used for other clothes.

In the preferred embodiment, the discontinuous perimeter stitching 22 defines first and second openings 24, 26 located at opposite ends of the nondisposable diaper. As shown in the drawings, the nondisposable diaper 10 according to the preferred embodiment comprises a wedge-shaped nondisposable diaper, having a wider end 28 and a narrower end 30, wherein the first opening 24 is located at the wider end 28 and the second opening 26 is located at the narrower end 30. It is noted that the wedged-shaped nondisposable diaper 10 according to the present invention is adapted to be used as an insert within a conventional diaper cover. It should be understood, however, that under the present invention, the diaper could be made in a variety of different shapes, including but not limited to wedged-shaped as shown, or hourglass shaped, rectangular shaped or other shapes adaptable to fit a baby's bottom. Also, the nondisposable diaper according to the present invention need not be an insert; it may be otherwise attachable with pins or other means for securing the diaper to the baby's bottom.

As best shown in FIGS. 2 and 5, the top section 12 further includes a top outside layer 32, a top inside layer 34, and a top absorbency pad 36 located between the top outside and inside layers 32, 34. In the preferred embodiment, the top section 12 further includes first top attachment means 38 for attaching the top absorbency pad 36 to the top inside layer 34. In the preferred embodiment, the first top attachment means 38 is enclosed within the top outside layer and thus protected from wear and tear associated with outside contact to the nondisposable diaper. The first top attachment means preferably comprises stitching 38 as shown in FIGS. 2 and 3. It should be understood that in alternative embodiments, the first attachment means could attach the absorbency pad to the top outside layer and still incorporate patentable features of the present invention. The top section 12 according to the preferred embodiment further includes a second top attachment means 40 for attaching the top outside layer 32 to the top inside layer 34.

The bottom section 14 includes a bottom outside layer 42, a bottom inside layer 44, and a bottom absorbency pad 46 located between the bottom outside and inside layers. The bottom section 14 further includes a first bottom attachment means 48 for attaching the absorbency pad 46 to the bottom inside layer 44, the attachment means being enclosed within the bottom outside layer 42 and thus protected from wear and tear from outside contact. The first bottom attachment means preferably comprises stitching 48 as shown in FIGS. 2. The bottom section 14 according to the preferred embodiment also includes a second bottom attachment means 50 for attaching the bottom outside layer 42 to the bottom inside layer 44.

As shown in FIGS. 2, 3 and 4, the top and bottom absorbency pads are smaller in size than the other layers and are centrally located where added absorbency is needed. It should be noted that the top and bottom absorbency pads 36, 46 need not be located between the respective top and bottom outside and inside layers. For example, in an alternative embodiment, the top and bottom absorbency pads could be attached to the inside surfaces 18 (i.e., the opposite sides of the top and bottom inside layers 34, 44) of the top and bottom sections.

In a preferred embodiment, the second top attachment means 40 and the second bottom attachment means 50 comprise continuous perimeter stitching as shown in FIGS. 1, 3 and 4. In an alternative preferred embodiment shown in FIG. 6, the second top and bottom attachment means 40, 50 and the means for attaching the top section 12 to the bottom section 14 comprise discontinuous perimeter stitching 22 which defines at least three openings: a first opening 24 between the top section 12 and the bottom section 14; a first top opening 52 between the top outside layer 32 and top inside layer 34; a first bottom opening 56 between the bottom outside layer 42 and the bottom inside layer 44. In the preferred embodiment, the discontinuous stitching 22 defines six openings, including the above listing openings: a second opening 26 between the top section 12 and bottom section 14; a second top opening 54 between the top outside layer 32 and the top inside layer 34; and a second bottom opening 58 between the bottom outside layer 42 and the bottom inside layer 44. These openings allow air to more freely flow between the various layers and sections and thereby permit the diaper to dry faster and more efficiently. Each opening should extend at least half the width of the end (i.e., of the wider end 28 or of the narrower end 30) on which the opening is located. This proportion for the openings provides improved dryability of the diaper without jeopardizing the integrity of the diaper's construction. For cost reasons, the manufacturer may, however, prefer to have each opening extend the entire width of the diaper end. It should be understood that the width of the opening may vary.

Several advantages should be noted in the present invention. First, the nondisposable diaper constructed according to the preferred embodiment provides two separate absorbency pads, as opposed to one thicker absorbency pad. This feature facilitates drying. Also, by providing air vents as described above, the absorbency pads are exposed to a more direct air flow.

FIGS. 3 and 4 are identified as top section 12. However, it should be understood that FIGS. 3 and 4 could also be used to describe bottom section 14 because, in the preferred embodiment, bottom section 14 mirrors the top section 12. For convenience, the top section will be referred to but it should be understood that FIGS. 3 and 4 also describe the bottom section 14. FIGS. 3 and 4 show that the absorbency pad 36 is enclosed between the top outside layer 32 and top inside layer 34. As shown, the stitching 38 does not penetrate the top outside layer 32 and therefor is protected against the wear and tear from outside contact. Thus, the critical seams associated with stitching 38 are not exposed for example to the baby's bottom. This feature also makes the nondisposable diaper more comfortable for the baby. Thus, the nondisposable diaper according to the present invention should be more durable and comfortable.

It is to be understood that, even though numerous characteristics and advantages of the present invention have been set forth in the foregoing description, together with details of the structure and function of the invention, the disclosure is illustrative only, and changes may be made in the detail, especially in matters of shape, size and arrangement of parts within the principles of the invention to the full extent indicated by the broad and general meaning of the terms in which the appended claims are expressed.

What is claimed is:

1. A nondisposable diaper comprising:
a top section having perimeter ends, and an inside surface and an outside surface;
a bottom section having perimeter ends, and an inside surface and an outside surface, the respective inside surfaces of the top and bottom sections facing one another; and
attachment means for attaching the top section to the bottom section along their respective perimeter ends in a discontinuous manner thus defining at least one opening between the respective top and bottom sections, the opening permitting air to more freely enter and flow between the respective inside surfaces of the top and bottom sections and thereby permitting the nondisposable diaper to dry faster;
wherein the top section comprises a top outside layer; a top inside layer; and top attachment means for attaching the top inside layer to the top outside layer; and wherein the top attachment means comprises continuous perimeter attachment means; the perimeter attachment means attaching respective perimeter ends of the top inside and outside layers.

2. A nondisposable diaper according to claim 1 wherein the attachment means comprises discontinuous perimeter stitching.

3. A nondisposable diaper according to claim 2 wherein the discontinuous perimeter stitching defines first and second openings located at opposite ends of the nondisposable diaper.

4. A nondisposable diaper according to claim 3 wherein the nondisposable diaper is wedge-shaped, having a wider end and a narrower end, the first opening located at the narrower end and the second opening located at the wider end.

5. A nondisposable diaper according to claim 4 wherein the first opening extends at least half the narrower end's width and the second opening extends at least half the wider end's width.

6. A nondisposable diaper according to claim 4 wherein the first opening extends approximately the narrower end's width and the second opening extends approximately the wider end's width.

7. A nondisposable diaper according to claim 1 further comprising means for providing additional absorbency to the nondisposable diaper, the absorbency means being located between the top section and bottom section.

8. A nondisposable diaper according to claim 7 wherein the absorbency means comprises an absorbency pad.

9. A nondisposable diaper according to claim 7 wherein the absorbency means comprises:
an inside layer having perimeter ends and being located and secured between the top and bottom sections;
an absorbency pad; and
second attachment means for attaching the absorbency pad to the inside layer, the second attachment means being enclosed between the top and bottom sections and does not penetrate either of said outside surfaces and thus is protected from wear and tear from outside contact to the nondisposable diaper.

10. A nondisposable diaper according to claim 1 wherein the top attachment means comprises discontinuous perimeter stitching, the perimeter stitching attaching respective perimeter ends of the inside and outside layers and defining at least one top opening between the top inside and outside layers, the top opening permitting air to more freely flow between the top inside and outside layers, thereby permitting the nondisposable diaper to dry faster.

11. A nondisposable diaper according to claim 1 wherein the top attachment means and the attachment means for attaching the top section and the bottom section comprise discontinuous perimeter stitching.

12. A nondisposable diaper according to claim 1 wherein the top section further comprises:
an absorbency pad located between the outside and inside layers; and
second top attachment means for attaching the absorbency pad to the top inside layer, the second top attachment means being enclosed between the top outside layer without penetrating the top outside layer and thus protected from wear and tear from outside contact to the nondisposable diaper.

13. A nondisposable diaper according to claim 12 wherein the top attachment means comprises continuous perimeter stitching, the perimeter stitching attaching respective perimeter ends of the top inside and outside layer.

14. A nondisposable diaper according to claim 12 wherein the top attachment means comprises discontinuous perimeter stitching, the perimeter stitching attaching respective perimeter ends of the top inside and outside layers and defining at least one top opening between the top inside and outside layers, the top opening permitting air to more freely flow between the top inside and outside layers, thereby permitting the nondisposable diaper to dry faster.

15. A nondisposable diaper comprising:
a top section having perimeter ends, and an inside surface and an outside surface, the top section further comprising a top outside layer, a top inside layer, a top absorbency pad located between the top outside and inside layers, top attachment means for attaching the top absorbency pad to the top inside layer;
a bottom section having perimeter ends, and an inside surface and an outside surface, the respective inside surfaces of the top and bottom sections facing one another; and
attachment means for attaching the top section to the bottom section along their respective perimeter ends;
wherein the top attachment means is enclosed between the respective outside surfaces of the top and bottom sections so that the attachment means does not penetrate either of said outside surfaces and is protected against wear and tear from outside contact to the top or bottom sections, further so that the attachment means is not directly exposed to a baby's skin, thus providing a more comfortable fit, and further so that the attachment means is not directly exposed to solid waste from the baby, thus making the nondisposable diaper easier to clean.

16. A nondisposable diaper according to claim 15 wherein the bottom section further comprises a bottom outside layer, a bottom inside layer, a bottom absorbency pad located between the bottom outside and inside layers, bottom attachment means for attaching the bottom absorbency pad to the top inside layer, the bottom attachment means being enclosed between the bottom outside layer without penetrating the bottom outside layer and thus protected from wear and tear from outside contact to the nondisposable diaper.

17. A nondisposable diaper according to claim 16 wherein the attachment means comprises discontinuous perimeter stitching, the stitching defining at least three openings: an opening between the respective top and bottom sections, a top opening between the top outside and inside layers, and a bottom opening between the bottom outside and inside layers, the three openings permitting the nondisposable diaper to dry faster.

18. A nondisposable diaper according to claim 17 wherein the discontinuous perimeter stitching defines first and second openings between the top and bott m sections, first and second top openings between the top outside and inside layers, and first and second bottom openings between the bottom outside and inside layers.

19. A nondisposable diaper according to claim 18 wherein the nondisposable diaper is wedge-shaped, having a wider end and a narrower end.

20. A nondisposable diaper comprising:

a top section having perimeter ends, and an inside surface and an outside surface, the top section further comprising a top outside layer, a top inside layer, a top absorbency pad located between the top outside and inside layers, a first top attachment means for attaching the absorbency pad to the top inside layer, and a second top attachment means for attaching the top outside layer to the top inside layer; and a bottom section having perimeter ends, and an inside surface and an outside surface, the bottom section further comprising a bottom outside layer, a bottom inside layer, a bottom absorbency pad located between the bottom outside and inside layers, a first bottom attachment means for attaching the absorbency pad to the bottom inside layer, a second bottom attachment means for attaching the bottom outside layer to the bottom inside layer; and attachment means for attaching the top section to the bottom section of their respective perimeter ends;

wherein the top and bottom attachment means are enclosed between the respective outside surfaces of the top and bottom sections so that the attachment means does not penetrate either of said outside surfaces and is protected against wear and tear from outside contact to the top or bottom sections, further so that the attachment means is not directly exposed to a baby's skin, thus providing a more comfortable fit, and further so that the attachment means is not directly exposed to solid waste from the baby, thus making the nondisposable diaper easier to clean.

21. A nondisposable diaper according to claim 20 wherein the attachment means comprises discontinuous perimeter stitching, the stitching defining at least one opening between the respective perimeter ends, the opening permitting air to more freely enter and flow between the respective inside surfaces of the top and bottom sections and thereby permitting the diaper to dry faster.

22. A nondisposable diaper according to claim 20 wherein the attachment means, the second top attachment means and the second bottom attachment means comprises discontinuous perimeter stitching, the stitching defining at least three openings, a first opening between the top section and the bottom section, a second opening between the top outside and inside layers, and a third opening between the botton outside and inside layers, the openings permitting the nondisposable diaper to dry faster.

23. A nondisposable diaper according to claim 20 wherein the attachment mean for attaching the top and bottom sections comprises continuous perimeter stitching and the second top and bottom attachment means comprises discontinuous perimeter stitching.

* * * * *